(12) United States Patent
Inouye et al.

(10) Patent No.: US 8,394,603 B2
(45) Date of Patent: Mar. 12, 2013

(54) CODON-OPTIMIZED NUCLEIC ACID FOR CODING APO-CLYTIN-II AND METHOD FOR USING THE SAME

(75) Inventors: Satoshi Inouye, Kanagawa (JP); Yuiko Sahara, Kanagawa (JP); Junichi Sato, Kanagawa (JP)

(73) Assignee: JNC Corporation, Tokyo (JP)

( * ) Notice: Subject to any disclaimer, the term of this patent is extended or adjusted under 35 U.S.C. 154(b) by 410 days.

(21) Appl. No.: 12/694,549

(22) Filed: Jan. 27, 2010

(65) Prior Publication Data

US 2010/0273202 A1    Oct. 28, 2010

(30) Foreign Application Priority Data

Jan. 29, 2009  (JP) ................................. 2009-018339

(51) Int. Cl.
- *C12Q 1/02* (2006.01)
- *C07H 21/04* (2006.01)
- *C07K 14/435* (2006.01)

(52) U.S. Cl. ...... 435/29; 435/69.1; 435/325; 435/320.1; 530/350; 536/23.5

(58) Field of Classification Search ........................ None
See application file for complete search history.

(56) References Cited

U.S. PATENT DOCUMENTS

| 5,714,666 | A | 2/1998 | Pritchett et al. | |
| 7,601,805 | B2 * | 10/2009 | Foti et al. | 530/350 |
| 2004/0171005 | A1 * | 9/2004 | Printen et al. | 435/6 |
| 2007/0275377 | A1 * | 11/2007 | Golz et al. | 435/6 |

FOREIGN PATENT DOCUMENTS

JP  2005-506053  3/2005

OTHER PUBLICATIONS

Cloning, Expression, Purification and Characterization of an Isotype of Clytin, a Calcium-Binding Photo-protein from the Luminous Hydromedusa Clytia gregarium) J. Biochem. 143, 711-717 (2008.*
Levine et al (Isolation and characterization of a photo-protein, "phialidin," and a spectrally unique green-fluorescent protein from the bioluminescent jellyfish Phialidium gregarium. Journal: Comparative Biochemistry and Physiology, vol. 72B, Issue 1, 1982, pp. 77-85, 1982).*
Vysotski et al. (Calcium-regulated Photo-proteins of Marine Coelenterates. Molecular Biology, 2006, vol. 40, No. 3, pp. 355-367).*
Inouye et al (Cloning and sequence analysis of cDNA for the Ca2+-activated photo-protein, clytin FEBS vol. 315, No. 3, 343-346, 1993.*
Inouye et al Expression, purification and characterization of photo-protein, clytin, from Clytia gregarium. Protein Expression and Purification 53 (2007) 384-389).*
Leonard D. Levine et al., "Isolation and Characterization of a Photoprotein, Phialdin, and a Spectrally Unique Green-Fluorescent Protein from the Bioluminescent Jellyfish Phialidium Gregarium" Comparative Biochemistry and Physiology, vol. 72B, Issue 1, 1982, pp. 77-85, 1982.
Satoshi Inouye et al., "Cloning and sequence analysis of cDNA for the $Ca^{2+}$-activated photoprotein, clytin" FEBS Letters, vol. 315, Issue 3, Jan. 11, 1993, pp. 343-346.
Satoshi Inouye, "Cloning, Expression, Purification and Characterization of an Isotype of Clytin, a Calcium-Binding Photoprotein from the Luminous Hydromedusa Clytia gregarium" The Japanese Biochemical Society, 2008, vol. 143, No. 5, pp. 711-717.

* cited by examiner

*Primary Examiner* — Kagnew H Gebreyesus
(74) *Attorney, Agent, or Firm* — J.C. Patents

(57) ABSTRACT

A codon-optimization of nucleic acid for coding apo-clytin-II protein is provided. Luminescent activity of clytin-II is remarkably enhanced. Accordingly, compared with the conventional use of the wild-type clytin-II, an intracellular calcium ion can be detected much more easily.

5 Claims, 1 Drawing Sheet

SEQUENCE LISTING

```
<160> NUMBER OF SEQ ID NOS: 12

<210> SEQ ID NO 1
<211> LENGTH: 189
<212> TYPE: PRT
<213> ORGANISM: Clytia gregaria

<400> SEQUENCE: 1

Val Lys Leu Asp Pro Asp Phe Ala Asn Pro Lys Trp Ile Asn Arg His
 1               5                  10                  15

Lys Phe Met Phe Asn Phe Leu Asp Ile Asn Gly Asn Gly Lys Ile Thr
                20                  25                  30

Leu Asp Glu Ile Val Ser Lys Ala Ser Asp Asp Ile Cys Ala Lys Leu
            35                  40                  45

Asp Ala Thr Pro Glu Gln Thr Lys Arg His Gln Asp Ala Val Glu Ala
        50                  55                  60

Phe Phe Lys Lys Met Gly Met Asp Tyr Gly Lys Glu Val Ala Phe Pro
65                  70                  75                  80

Glu Phe Ile Lys Gly Trp Glu Glu Leu Ala Glu His Asp Leu Glu Leu
                85                  90                  95

Trp Ser Gln Asn Lys Ser Thr Leu Ile Arg Glu Trp Gly Asp Ala Val
               100                 105                 110

Phe Asp Ile Phe Asp Lys Asp Ala Ser Gly Ser Ile Ser Leu Asp Glu
           115                 120                 125

Trp Lys Ala Tyr Gly Arg Ile Ser Gly Ile Cys Pro Ser Asp Glu Asp
       130                 135                 140

Ala Glu Lys Thr Phe Lys His Cys Asp Leu Asp Asn Ser Gly Lys Leu
145                 150                 155                 160

Asp Val Asp Glu Met Thr Arg Gln His Leu Gly Phe Trp Tyr Thr Leu
               165                 170                 175

Asp Pro Thr Ser Asp Gly Leu Tyr Gly Asn Phe Val Pro
           180                 185
```

<210> SEQ ID NO 2
<211> LENGTH: 570
<212> TYPE: DNA
<213> ORGANISM: Clytia gregaria

<400> SEQUENCE: 2

```
gtcaaactcg atcctgattt tgcaaatcca aaatggatca acagacacaa atttatgttc      60 aacttttttgg acataaacgg taatgggaaa atcacattag atgaaatcgt ctccaaagct    120
tcagacgaca tttgtgctaa actggatgca acaccagaac agaccaaacg tcaccaggat    180
gctgttgaag cgttttttcaa gaaaatgggc atggattatg gtaaagaagt tgcattccca    240
gaatttatta agggatggga agagttggcc gaacacgact tggaactctg gctctaaaac    300
aaaagtacat tgatccgtga atggggagat gctgttttcg acattttcga caaagacgca    360
agtggctcaa tcagtttaga cgaatggaag gcttacggac gaatctctgg aatctgtcca    420
tcagacgaag acgctgagaa gacgttcaaa cattgtgatt tggacaacag tggcaaactt    480
gatgttgatg agatgaccag gcaacattta ggcttctggt acacattgga tccaacttct    540
gatggtcttt atgcaatttt tgttccctaa                                    570
```

<210> SEQ ID NO 3
<211> LENGTH: 570
<212> TYPE: DNA
<213> ORGANISM: Clytia gregaria

<400> SEQUENCE: 3

```
gtgaagctgg accccgactt cgccaacccc aagtggatca acagacacaa gttcatgttc      60
aacttcctgg acatcaacgg caacggcaag atcaccctgg acgagatcgt gagcaaggcc    120
agcgacgaca tctgcgccaa gctggacgcc accccccgagc agaccaagag acaccaggac    180
gccgtggagg ccttcttcaa gaagatgggc atggactacg gcaaggaggt ggccttcccc    240
gagttcatca agggctggga ggagctggcc gagcacgacc tggagctgtg gagccagaac    300
aagagcaccc tgatcagaga gtggggcgac gccgtgttcg acatcttcga caaggacgcc    360
agcggcagca tcagcctgga cgagtggaag gcctacggca gaatcagcgg catctgcccc    420
agcgacgagg acgccgagaa gaccttcaag cactgcgacc tggacaacag cggcaagctg    480
gacgtggacg agatgaccag acagcacctg ggcttctggt acaccctgga ccccaccagc    540
gacggcctgt acggcaactt cgtcccctaa                                    570
```

<210> SEQ ID NO 4
<211> LENGTH: 591
<212> TYPE: DNA
<213> ORGANISM: Clytia gregaria
<220> FEATURE:
<221> NAME/KEY: CDS
<222> LOCATION: (1)..(591)
<223> OTHER INFORMATION:

<400> SEQUENCE: 4

```
atg ctc gag ctg cag gaa ttc gtg aag ctg gac ccc gac ttc gcc aac       48
Met Leu Glu Leu Gln Glu Phe Val Lys Leu Asp Pro Asp Phe Ala Asn
1               5                   10                  15 ccc aag tgg atc aac aga cac aag ttc atg ttc aac ttc ctg gac atc       96
Pro Lys Trp Ile Asn Arg His Lys Phe Met Phe Asn Phe Leu Asp Ile
            20                  25                  30 aac ggc aac ggc aag atc acc ctg gac gag atc gtg agc aag gcc agc      144
Asn Gly Asn Gly Lys Ile Thr Leu Asp Glu Ile Val Ser Lys Ala Ser
        35                  40                  45 gac gac atc tgc gcc aag ctg gac gcc acc ccc gag cag acc aag aga      192
Asp Asp Ile Cys Ala Lys Leu Asp Ala Thr Pro Glu Gln Thr Lys Arg
```

```
Asp Asp Ile Cys Ala Lys Leu Asp Ala Thr Pro Glu Gln Thr Lys Arg
    50                  55                  60 cac cag gac gcc gtg gag gcc ttc ttc aag aag atg ggc atg gac tac    240
His Gln Asp Ala Val Glu Ala Phe Phe Lys Lys Met Gly Met Asp Tyr
 65                  70                  75                  80 ggc aag gag gtg gcc ttc ccc gag ttc atc aag ggc tgg gag gag ctg    288
Gly Lys Glu Val Ala Phe Pro Glu Phe Ile Lys Gly Trp Glu Glu Leu
                 85                  90                  95 gcc gag cac gac ctg gag ctg tgg agc cag aac aag agc acc ctg atc    336
Ala Glu His Asp Leu Glu Leu Trp Ser Gln Asn Lys Ser Thr Leu Ile
            100                 105                 110 aga gag tgg ggc gac gcc gtg ttc gac atc ttc gac aag gac gcc agc    384
Arg Glu Trp Gly Asp Ala Val Phe Asp Ile Phe Asp Lys Asp Ala Ser
        115                 120                 125 ggc agc atc agc ctg gac gag tgg aag gcc tac ggc aga atc agc ggc    432
Gly Ser Ile Ser Leu Asp Glu Trp Lys Ala Tyr Gly Arg Ile Ser Gly
    130                 135                 140 atc tgc ccc agc gac gag gac gcc gag aag acc ttc aag cac tgc gac    480
Ile Cys Pro Ser Asp Glu Asp Ala Glu Lys Thr Phe Lys His Cys Asp
145                 150                 155                 160 ctg gac aac agc ggc aag ctg gac gtg gac gag atg acc aga cag cac    528
Leu Asp Asn Ser Gly Lys Leu Asp Val Asp Glu Met Thr Arg Gln His
                165                 170                 175 ctg ggc ttc tgg tac acc ctg gac ccc acc agc gac ggc ctg tac ggc    576
Leu Gly Phe Trp Tyr Thr Leu Asp Pro Thr Ser Asp Gly Leu Tyr Gly
            180                 185                 190 aac ttc gtc ccc taa                                                591
Asn Phe Val Pro
            195

<210> SEQ ID NO 5
<211> LENGTH: 669
<212> TYPE: DNA
<213> ORGANISM: Clytia gregaria

<400> SEQUENCE: 5
atgaaaaaga cagctatcgc gattgcagtg gcactggctg gtttcgctac cgtagcgcag      60
gccgcgaatt cccaccatca ccatcaccat ggtaagcttg tgaagctgga ccccgacttc     120
gccaacccca gtggatcaa cagacacaag ttcatgttca acttcctgga catcaacggc     180
aacggcaaga tcaccctgga cgagatcgtg agcaaggcca gcgacgacat ctgcgccaag     240
ctggacgcca cccccgagca gaccaagaga caccaggacg ccgtggaggc cttcttcaag     300
aagatgggca tggactacgg caaggaggtg gccttccccg agttcatcaa gggctgggag     360
gagctggccg agcacgacct ggagctgtgg agccagaaca gagcacccct gatcagagag     420
tggggcgacg ccgtgttcga catcttcgac aaggacgcca gcggcagcat cagcctggac     480
gagtggaagg cctacggcag aatcagcggc atctgcccca gcgacgagga cgccgagaag     540
accttcaagc actgcgacct ggacaacagc ggcaagctgg acgtggacga gatgaccaga     600
cagcacctgg gcttctggta caccctggac cccaccagcg acggcctgta cggcaacttc     660
gtcccctaa                                                              669

<210> SEQ ID NO 6
<211> LENGTH: 669
<212> TYPE: DNA
<213> ORGANISM: Clytia gregaria
<220> FEATURE:
<221> NAME/KEY: CDS
<222> LOCATION: (1)..(669)
<223> OTHER INFORMATION:
```

<400> SEQUENCE: 6

```
atg aaa aag aca gct atc gcg att gca gtg gca ctg gct ggt ttc gct      48
Met Lys Lys Thr Ala Ile Ala Ile Ala Val Ala Leu Ala Gly Phe Ala
1               5                   10                  15 acc gta gcg cag gcc gcg aat tcc cac cat cac cat cac cat ggt aag      96
Thr Val Ala Gln Ala Ala Asn Ser His His His His His His Gly Lys
                20                  25                  30 ctt gtg aag ctg gac ccc gac ttc gcc aac ccc aag tgg atc aac aga     144
Leu Val Lys Leu Asp Pro Asp Phe Ala Asn Pro Lys Trp Ile Asn Arg
            35                  40                  45 cac aag ttc atg ttc aac ttc ctg gac atc aac ggc aac ggc aag atc     192
His Lys Phe Met Phe Asn Phe Leu Asp Ile Asn Gly Asn Gly Lys Ile
        50                  55                  60 acc ctg gac gag atc gtg agc aag gcc agc gac gac atc tgc gcc aag     240
Thr Leu Asp Glu Ile Val Ser Lys Ala Ser Asp Asp Ile Cys Ala Lys
65                  70                  75                  80 ctg gac gcc acc ccc gag cag acc aag aga cac cag gac gcc gtg gag     288
Leu Asp Ala Thr Pro Glu Gln Thr Lys Arg His Gln Asp Ala Val Glu
                85                  90                  95 gcc ttc ttc aag aag atg ggc atg gac tac ggc aag gag gtg gcc ttc     336
Ala Phe Phe Lys Lys Met Gly Met Asp Tyr Gly Lys Glu Val Ala Phe
            100                 105                 110 ccc gag ttc atc aag ggc tgg gag gag ctg gcc gag cac gac ctg gag     384
Pro Glu Phe Ile Lys Gly Trp Glu Glu Leu Ala Glu His Asp Leu Glu
        115                 120                 125 ctg tgg agc cag aac aag agc acc ctg atc aga gag tgg ggc gac gcc     432
Leu Trp Ser Gln Asn Lys Ser Thr Leu Ile Arg Glu Trp Gly Asp Ala
130                 135                 140 gtg ttc gac atc ttc gac aag gac gcc agc ggc agc atc agc ctg gac     480
Val Phe Asp Ile Phe Asp Lys Asp Ala Ser Gly Ser Ile Ser Leu Asp
145                 150                 155                 160 gag tgg aag gcc tac ggc aga atc agc ggc atc tgc ccc agc gac gag     528
Glu Trp Lys Ala Tyr Gly Arg Ile Ser Gly Ile Cys Pro Ser Asp Glu
                165                 170                 175 gac gcc gag aag acc ttc aag cac tgc gac ctg gac aac agc ggc aag     576
Asp Ala Glu Lys Thr Phe Lys His Cys Asp Leu Asp Asn Ser Gly Lys
            180                 185                 190 ctg gac gtg gac gag atg acc aga cag cac ctg ggc ttc tgg tac acc     624
Leu Asp Val Asp Glu Met Thr Arg Gln His Leu Gly Phe Trp Tyr Thr
        195                 200                 205 ctg gac ccc acc agc gac ggc ctg tac ggc aac ttc gtc ccc taa        669
Leu Asp Pro Thr Ser Asp Gly Leu Tyr Gly Asn Phe Val Pro
    210                 215                 220
```

<210> SEQ ID NO 7
<211> LENGTH: 36
<212> TYPE: DNA
<213> ORGANISM: Artificial
<220> FEATURE:
<223> OTHER INFORMATION: Designed for primer production

<400> SEQUENCE: 7
gtaccaccat gctcgagctg caggaattct ctagag                              36

<210> SEQ ID NO 8
<211> LENGTH: 36
<212> TYPE: DNA
<213> ORGANISM: Artificial
<220> FEATURE:
<223> OTHER INFORMATION: Designed for primer production

```
<400> SEQUENCE: 8
tcgactctag agaattcctg cagctcgagc atggtg                                      36

<210> SEQ ID NO 9
<211> LENGTH: 30
<212> TYPE: DNA
<213> ORGANISM: Artificial
<220> FEATURE:
<223> OTHER INFORMATION: Designed for primer production

<400> SEQUENCE: 9
agcttctgca ggtcgactct agactcgagg                                             30

<210> SEQ ID NO 10
<211> LENGTH: 30
<212> TYPE: DNA
<213> ORGANISM: Artificial
<220> FEATURE:
<223> OTHER INFORMATION: Designed for primer production

<400> SEQUENCE: 10
gatccctcga gtctagagtc gacctgcaga                                             30

<210> SEQ ID NO 11
<211> LENGTH: 30
<212> TYPE: DNA
<213> ORGANISM: Artificial
<220> FEATURE:
<223> OTHER INFORMATION: Designed for primer production

<400> SEQUENCE: 11
ggcaagcttg tgaagctgga ccccgacttc                                             30

<210> SEQ ID NO 12
<211> LENGTH: 30
<212> TYPE: DNA
<213> ORGANISM: Artificial
<220> FEATURE:
<223> OTHER INFORMATION: Designed for primer production

<400> SEQUENCE: 12
ggcctcgagt tagggacga agttgccgta                                              30
```

CODON-OPTIMIZED NUCLEIC ACID FOR CODING APO-CLYTIN-II AND METHOD FOR USING THE SAME

CROSS-REFERENCE TO RELATED APPLICATION

This application claims the priority benefit of Japan application serial no. 2009-018339, filed on Jan. 29, 2009. The entirety of the above-mentioned patent application is hereby incorporated by reference herein and made a part of specification.

BACKGROUND OF THE INVENTION

1. Field of the Invention

The present invention generally relates to a codon-optimized nucleic acid for coding apo-clytin-II protein, apo-clytin-II protein, and method for preparing the same.

2. Description of Related Art

In the luminescent jellyfish of coelenterates, six photoproteins are now known to emit light by specifically binding to calcium ions. Among these proteins, aequorin and obelin have been studied in detail. These calcium-binding photoproteins have been used as a biological calcium indicator and for determining calcium concentration in cells. Furthermore, these proteins have been used in the following process. By using the gene of the protein, information about the important modifier and the biological mechanism in the cellular environment that are dependent upon calcium is deduced.

The photoprotein clytin was isolated from other luminous jellyfish, *Clytia gregaria*, in 1982 (see Non-patent Reference 1). Its gene was isolated in 1993, and it was confirmed that the gene could be expressed in *E. coli* (see Non-patent Reference 2). Thereafter, gene analysis was performed in detail by Inouye et al., and new gene was identified as new clytin with different luminescence property. The new gene from *Clytia gregaria* was named as clytin-II to distinguish from the previously isolated clytin (=clytin-I) (see Non-patent Reference 3). The clytin-II gene can be expressed in *E. coli*, and can be purified as recombinant clytin-II, which exhibits a potential application in the determination of a biological calcium indicator or the calcium concentration.

Compared with aequorin and clytin-I, the luminescence capacity of the total light emission per protein of clytin-II is almost the same; however, the initial luminescence intensity of clytin-II is about five times higher. Thus, the S/N ratio of clytin-II is five times higher than that of aequorin and clytin-I, which indicates that clytin-II may be superior to aequorin and clytin-I when used in a detection system.

Clytin-II having the luminescence ability is a complex containing apo-clytin-II protein with a molecular weight of about 22,000 and coelenterazine binding molecular oxygen. A molecule of the clytin-II protein has three sequences that can bind calcium ion. When clytin-II is bound to calcium ion, blue light ($\lambda max=470$ nm) is emitted, and carbon dioxide and coelenteramide are generated. Since the luminescence intensity is dependent on the concentration of calcium ion, clytin-II can be used to determine the calcium concentration with high sensitivity.

According to the prior art, the amino acid sequence of the photoprotein clytin-II is initially published by Inouye (see Non-patent Reference 3), and is disclosed in the EMBL sequence database under accession number AB360785 (disclosed as SEQ ID NO: 1 in this specification).

Amino acid sequence identity between clytin-II and other photoproteins, clytin-I, aequorin, obelin, and mitrocomin, is 88.4%, 61.9%, 76.2%, 60.8% respectively, while the identity with aequorin, obelin, and mitrocomin is low (see Non-patent Reference 3).

Furthermore, in Japanese Patent Publication 2005-506053, a codon-optimized (humanized) gene sequence based on the amino acid sequence of the photoprotein aequorin is reported. The amino acid sequence homology of codon-optimized aequorin with clytin-II shows 61.9% identity, and the luminescence pattern is different from clytin-II. Further, the nucleotide sequence identity between aequorin and clytin-II is 64.6%, so aequorin and clytin-II can be identified as totally different functional molecules.

PRIOR ART REFERENCES

[Patent Reference]
[Patent Reference 1] Japanese Patent Publication 2005-506053
[Non-patent References]
[Non-patent Reference 1] Comp. Biochem. Physiol. (1982) 72B, 77-85
[Non-patent Reference 2] FEBS Lett. (1993) 333, 301-305
[Non-patent Reference 3] J. Biochem. 143 (2008) 711-717

SUMMARY OF THE INVENTION

Currently there is no actual evidence on stable expression of recombinant clytin-II in eukaryotic cells or a host assay cell. There is also no actual result on the use of clytin-II as a reporter protein for detecting the change of intracellular calcium concentration. Furthermore, there is no study on the usefulness of clytin-II in the screening of small molecules that stimulate G protein-coupled receptor and/or ion channel. Moreover, there is no report on the optimized clytin-II sequence.

When analyzing the change of intracellular calcium concentration in mammalian cells with clytin-II, it is necessary to introduce a plasmid containing a nucleic acid for coding apo-clytin-II into cells. The introduction of nucleic acids into cells can be achieved by the following standard transfection technology: formation of DNA complex with ionic lipid reagent, or precipitation with $CaPO_4$.

However, in the transformed mammalian cells, when merely a small amount of cell groups contain the apo-clytin-II expressing plasmid, the expression level of apo-clytin-II protein is low. As a result, in a calcium analysis using clytin-II regenerated from apo-clytin-II, the application of clytin-II is limited due to low luminescence intensity (low light emission). The inventors of the present invention set forth the following hypothesis based on this fact: the increase in the intracellular expression of apo-clytin-II protein can effectively achieve higher light emission and signal to noise ratio in a calcium analysis.

Furthermore, the inventors of the present invention focus on the following aspects. The increase of apo-clytin-II gene transcription allows the performance of the calcium analysis in a mammalian cell, which is difficult to achieve with the standard transduction technology. The amplification can be achieved by introducing apo-clytin-II gene via the retrovirus gene delivery method, or other methods in which the number of transcribed genes is generally less than that of transiently transduced genes. Further, the gene delivery to a wider range of mammalian cells can be achieved.

Moreover, the inventors of the present invention have not identify any publication regarding a codon-optimized version with increased expression on apo-clytin-II protein in mammalian cells, and the use of the same.

Therefore, the inventors of the present invention have conducted extensive researches on the problems above in the prior art. As a result, the inventors have found that codon optimization (hereinafter known as humanization) of a nucleic acid for coding apo-clytin-II protein can significantly improve the luminescent activity of clytin-II; thus, the detection of intracellular calcium ion is easier, compared with that using wild-type clytin-II in the prior art. The inventors have completed the invention based on the above-observations.

The present invention includes at least the following features.

(1) A codon-optimized nucleic acid is for coding apo-clytin-II protein.

(2) The codon-optimized nucleic acid according to Item 1 is for coding apo-clytin-II protein having an amino acid sequence of SEQ ID NO: 1, or a variant thereof.

(3) A codon-optimized nucleic acid is formed by fusing the codon-optimized nucleic acid according to Item 1 or 2 with a nucleic acid for coding other proteins.

(4) The codon-optimized nucleic acid according to any one of Items 1 to 3 includes one or more codon selected from the group consisting of codon for coding CGC arginine, codon for coding AAC asparagine, codon for coding GAC aspartic acid, codon for coding CAG glutamine, codon for coding GAG glutamic acid, codon for coding GGC glycine, codon for coding CAC histidine, codon for coding ATC isoleucine, codon for coding CTG leucine, codon for coding AAG lysine, codon for coding CCC proline, codon for coding TTC phenylalanine, codon for coding TCC or AGC serine, codon for coding TAC tyrosine, and codon for coding GTG valine, and the number of the one or more codon is greater than that of a nucleic acid for coding wild-type jellyfish apo-clytin-II protein of SEQ ID NO: 2.

(5) An apo-clytin-II protein is expressed by the codon-optimized nucleic acid according to any one of Items 1 to 4.

(6) A clytin-II includes the apo-clytin-II of Item 5 as a component.

(7) An expression vector, wherein the position of its codon-optimized nucleic acid for coding apo-clytin-II protein is under the regulatory control of a promoter that functions in mammalian cells.

(8) The expression vector according to Item 7 includes the codon-optimized nucleic acid for coding apo-clytin-II protein, and a regulatory sequence for controlling the expression of the codon-optimized nucleic acid for coding apo-clytin-II protein in mammalian cells.

(9) A recombinant host cell includes a codon-optimized nucleic acid for coding apo-clytin-II protein.

(10) In the recombinant host cell according to Item 9, the host cell is a mammalian cell.

(11) In the recombinant host cell according to Item 9, the host cell is a human cell.

(12) In the recombinant host cell according to Item 9, the host cell is a non-human mammalian cell.

(13) A method for preparing apo-clytin-II protein includes the steps of:
(i) preparing a recombinant expression vector that allows a codon-optimized nucleic acid for coding apo-clytin-II protein to be under the regulatory control of a promoter that can function in a host cell;
(ii) introducing the recombinant expression vector into the host cell; and
(iii) culturing the host cell, for expressing the apo-clytin-II protein.

(14) A method for enhancing the luminescence intensity of clytin-II includes combining a codon-optimized nucleic acid for coding apo-clytin-II protein with a regulatory nucleic acid for expressing the codon-optimized nucleic acid to form a nucleic acid, and introducing the resulting nucleic acid into a host cell.

(15) An application of a codon-optimized nucleic acid for coding apo-clytin-II protein, for enhancing the luminescence intensity of clytin-II in host cells.

(16) A method for determining the capability of a compound for inhibiting a receptor through the change of intracellular calcium ion upon activation includes contacting a host cell genetically engineered to express apo-clytin-II protein with coelenterazine or a derivative of coelenterazine, and then determining the amount of the generated light.

(17) The method according to Item 16 further includes recording the capability of inhibiting the receptor.

EFFECT OF THE INVENTION

The codon-optimized nucleic acid for coding apo-clytin-II is a novel substance, and the humanized apo-clytin-II protein (hereinafter sometimes known as "codon-optimized apo-clytin-II protein") obtained by introducing the codon-optimized nucleic acid into a host cell exhibits a higher luminescent activity when forming a complex (humanized clytin-II) consisting of the luminescent substrate and molecular oxygen, compared with that using wild-type apo-clytin-II. Furthermore, the clytin-II obtained by the present invention is very effective in many applications, such as the detection of intracellular calcium ion.

In order to make the features and advantages of the present invention comprehensible, specific embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
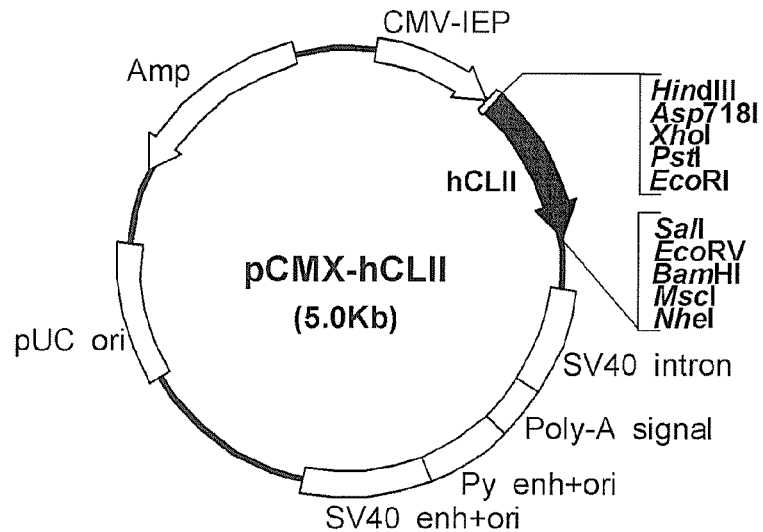
FIG. 1 is a schematic diagram of the codon-optimized apo-clytin-II protein expression vector pCMX-hCLII in eukaryotic organisms used in the present invention.

Reference will now be made in detail to the present embodiments of the invention, examples of which are illustrated in the accompanying drawings. Wherever possible, the same reference numbers are used in the drawings and the description to refer to the same or like parts.

The first aspect of the present invention is a codon-optimized nucleic acid for coding apo-clytin-II protein (hereinafter also referred as codon-optimized apo-clytin-II nucleic acid).

In preferred embodiments, the codon-optimized apo-clytin-II protein contains a sequence of SEQ ID NO: 1 or a truncated version thereof.

The truncated version is a protein in which one or more amino acids on or near the N-terminus or C-terminus are removed. In an embodiment, the truncated version is a protein with less than 50 amino acids being removed from the C-terminus. Herein, the truncated version is required to maintain several luminescence properties.

Another embodiment includes variants of apo-clytin-II protein of wild-type apo-protein disclosed by Inouye (J. Biochem. 143 (2008) 711-717). Herein, the variants include enhanced or modified luminescence property. Further, the variants are preferably amino acid substitutions based on the sequence expressed by SEQ ID NO: 1, or variants obtained from the wild-type amino acid sequence by changing one, two, or three amino acids. Examples of variants of the apo-clytin-II protein may include variant with valine at position 62 of SEQ ID NO 1 replaced by isoleucine, variant with alanine at position 78 replaced by proline, and variant with glutamic acid at position 91 replaced by lysine, and the like.

Furthermore, the sequence identity of variation sequences in the embodiments of the present invention with the sequence of SEQ ID NO: 1 is preferably 80% or more, 85% or more, 90% or more, 95% or more, 97% or more, 98% or more, and more preferably 99% or more. The sequence identity between two sequences can be evaluated by, for example, best computer alignment analysis with the appropriate software, such as NCBI Blast, WashU Blast2, Fasta, and PILEUP, or using a scoring matrix like Blosum62. Herein, the sequence identity between two sequences is determined by finding an approximation of the "gold-standard" alignment algorithm of Smith-Waterman.

The terms "codon-optimization" and "humanization" used in the specification refer to one or more replacement of codon of jellyfish apo-clytin-II with codon more frequently used in human genes, preferably a significant number of replacement, to adapt to the expression in mammalian cells, especially in human cells.

In another preferred embodiment, the percentage of humanized codon is preferably 10% or more, 20% or more, 30% or more, 40% or more, 50% or more, 60% or more, 70% or more, 80% or more, 90% or more, 95% or more, 98% or more, and more preferably 99% or more.

The codon-optimized nucleic acid of the present invention is generally cDNA, and can also contain genome copy.

The codon-optimized nucleic acid can be chemically synthesized by the standard techniques in the art, or obtained by mutation of wild-type genome or wild-type cDNA. Nucleotide variation or nucleotide mutation can be achieved by novel polynucleotide synthesis, polymerase chain reaction (PCR), site-directed mutagenesis using an appropriately designed oligonucleotide primer, or other methods known by those of ordinary skill in the art. The codon-optimized apo-clytin-II nucleic acid of the present invention can be designed to have an appropriate restriction enzyme recognition sequence at the terminus, or a restriction enzyme sequence with an additional base sequence can be used to facilitate the cloning of the humanized gene on a plasmid vector.

The codon-optimized apo-clytin-II protein-coding amino acid sequence can be expressed by various expression vector/host systems. The expression vector/host systems are not specifically limited, and include, for example, recombinant adeno-virus system, adeno-associated virus (AAV) system, or retrovirus system. The expression vectors useful in the present invention preferably include, for example, vaccinia virus, cytomegalo virus, herpes simplex virus, and defective hepatitis B virus. Herein, in order to express the codon-optimized apo-clytinII nucleic acid, a mammalian expression system is preferably used; however, other vectors and host cells, such as bacteria, yeast, plants, fungi and insects can also be used.

Expression vectors in a mammalian expression system generally include an origin of replication, a promoter, a transcription initiation site, optionally a signal peptide, a polyadenylation site, and a transcription termination site, and the like. The vectors generally also contain one or more antibiotics-resistant marker(s) for selection. An appropriate expression vector in the present invention may be plasmid, cosmid, phage, or virus, such as retrovirus. The coding sequence of the protein is placed under the control of an appropriate promoter (i.e., HSV, CMV, TK, RSV, SV40, etc.), regulatory factors, and transcription terminator, such that the nucleic acid coding the protein (hereinafter sometimes called "coding sequence") is transcribed into RNA in the host cell transformed or transduced with the expression vector.

The coding sequence may or may not contain a signal peptide or leader sequence for the secretion of the target protein out of the host cell. A vector useful in the present invention preferably contains at least one multiple cloning site. In an embodiment, there is a cloning site or a multiple cloning site situated between the promoter and the codon-optimized apo-clytin-II nucleic acid. The cloning site is in-frame since it is close to the codon-optimized apo-clytin-II nucleic acid; and thus, it can be used to generate an N-terminus fusion protein by cloning a second nucleic acid sequence at the cloning site. In another embodiment, there may be a cloning site or a multiple cloning site situated immediately downstream of the codon-optimized apo-clytin-II nucleic acid to facilitate the creation of C-terminus fusions in a similar fashion to that for N-terminus fusions described above.

The expression and purification of the codon-optimized apo-clytin-II protein of the present invention can be easily accomplished by the methods well-known in the art (for example, those described in "Molecular Cloning-A Laboratory Manual, second edition 1989" by Sambrook et al.). The use of expression vectors and plasmids is well-known to those of ordinary skill in the art. In almost all cases, any mammalian cell expression vector can be used in the expression of the codon-optimized apo-clytin-II protein of the present invention.

According to another aspect of the present invention, an expression vector containing a regulatory sequence capable of controlling the expression of a codon-optimized apo-clytin-II nucleic acid in host cells is provided.

In the expression vector of the present invention, the codon-optimized apo-clytin-II nucleic acid is preferably under the transcription regulation of a promoter that can function in mammalian cells.

The vectors containing a codon-optimized apo-clytin-II nucleic acid can be introduced, that is being transformed or transduced, into mammalian cells such as Chinese hamster ovary (CHO) cell, bacteria such as *E. coli*, yeasts such as *Saccharomyces cerevisiae* or *Pichia pastoris*, or other suitable hosts that can easily be subjected to operations such as mutagenesis, cloning, or expression. The implementation of the present invention is not dependent on any particular host cell line or vector, and is not limited thereby. The host cells or vectors useful in the present invention are known and can be selected by those of ordinary skill in the art.

The method for introducing vectors into cells is preferably those commonly used, and includes, for example, calcium phosphate method, electroporation method, microinjection method, diethylaminoethyl-dextran method (DEAE-dextran method), method using a liposome reagent, lipofection method using a cationic lipid. In the case of a cyclic vector, the vector can be linearized by a known method and then introduced into cells.

A host cell transformed or transduced with a vector containing a codon-optimized apo-clytin-II nucleic acid can be cultured under the conditions suitable for the expression of the target substance and the recovery of the target substance from cell culture. The expressed codon-optimized apo-clytin- II protein may be secreted into the culture or stored in the cell, depending on the sequences used, which is based on whether a suitable secretion signal sequence is present or not. Here, both transiently transformed cells/cell lines and stably transformed cells/cell lines are considered as objects of the research.

Suitable host cells for expressing the codon-optimized apo-clytin-II protein include, for example, CHO, COS, HeLa, BHK, Vero, MDCK, HepG2, HEK293, K562, etc.

In making a transgenic animal capable of expressing the codon-optimized apo-clytin-II protein, for example, an expression system disclosed in U.S. Pat. No. 5,714,666 can be used.

The present invention further provides a transgenic non-human animal, which contains a codon-optimized apo-clytin-II nucleic acid and a regulatory sequence for controlling the expression of the codon-optimized apo-clytin-II protein in the cell.

The transgenic animal is not particularly limited, and is preferably a mouse in the present invention.

In another aspect of the present invention, a host cell suitable for expressing the codon-optimized apo-clytin-II protein of the present invention is provided, which is a recombinant host cell containing a codon-optimized apo-clytin-II nucleic acid. According to the present invention, the host cell is not limited, and preferably is a mammalian cell. The mammalian cells include human cells and non-human cells, such as CHO-K1 and *Phoenix* cells. Among the mammalian cells, human cells are most preferred in the present invention.

The recombinant host cell according to an embodiment of the present invention generates the codon-optimized apo-clytin-II protein in a sufficient amount that can be detected when forming the clytin-II.

According to the codon usage frequency formed from the coding sequence of the wild-type clytin-II as shown in Table 1, the apo-clytin-II codon of the wild-type jellyfish at position 3 is preferably either A or U. Generally speaking, the residue at position 3 of the preferred mammalian codon is preferably C or G, and most preferably C, regardless the homology of the two residues at position 1 and position 2. Haas et al., (Current Biology. 6(3):3135-324, 1996) analyzed the comparison of 100 high-expression human genes, and the results showed the following tendencies. For example, 53% of the alanine (GCX) residue in the high-expression genes is coded by GCC, 17% is coded by GCT, 13% is coded by GCA, and 17% is coded by GCG. Similarly, the serine residue has the following statistics: TCC (28%), TCT (13%), TCA (5%), TCG (9%), AGC (34%), and AGT (10%). As shown in the table of the usage frequency of the codon among jellyfish and human being, in the amino acids with only two codons for selection, the wild-type jellyfish apo-clytin-II nucleic acid generally uses the most non-preferred codon compared to the preferred codon of human genes.

TABLE 1

Usage frequency of wild-type clytin-II codon
[Table 1]

| 1st base | 2nd base | | | | | | | | | 3rd base |
|---|---|---|---|---|---|---|---|---|---|---|
| | U | | C | | A | | G | | | |
| U | TTT Phe | 6 | TCT Ser | 3 | TAT Tyr | 2 | TGT Cys | 3 | | T |
| | TTC | 7 | TCC | 1 | TAC | | 2 | TGC end | 0 | C |
| | TTA Leu | 3 | TCA | 3 | TAA end | 0 | TGA Trp | 0 | | A |
| | TTG | 6 | TCG | 0 | TAG | 0 | TGG | 6 | | G |

TABLE 1-continued

Usage frequency of wild-type clytin-II codon
[Table 1]

| 1st base | 2nd base | | | | | | | | | 3rd base |
|---|---|---|---|---|---|---|---|---|---|---|
| | U | | C | | A | | G | | | |
| C | CTT | 2 | CCT Pro | 1 | CAT His | 2 | CGT Arg | 2 | | T |
| | CTC | 2 | CCC | 1 | CAC | 3 | CGC | | 0 | C |
| | CTA | 0 | CCA | 5 | CAA Gln | 2 | CGA | | 1 | A |
| | CTG | 1 | CCG | 0 | CAG | 2 | CGG | | 0 | G |
| A | ATT Ile | 3 | ACT Thr | 1 | AAT Asn | 3 | AGT Ser | 4 | | T |
| | ATC | 7 | ACC | 2 | AAC | 5 | AGC | | 0 | C |
| | ATA | 1 | ACA | 4 | AAA Lys | 13 | AGA Arg | 1 | | A |
| | ATG Met | 4 | ACG | 1 | AAG | 4 | AGG | | 1 | G |
| G | GTT Val | 5 | GCT Ala | 6 | GAT Asp | 12 | GGT Gly | 3 | | T |
| | GTC | 2 | GCC | 1 | GAC | 11 | GGC | | 5 | C |
| | GTA | 0 | GCA | 4 | GAA Glu | 11 | GGA | | 4 | A |
| | GTG | 0 | GCG | 1 | GAG | 3 | GGG | | 1 | G |

In constructing a codon-optimized apo-clytin-II nucleic acid, each codon is replaced by either C or G at the third position; thus, each codon is converted into mammalian equivalents. If this cannot be accomplished, it is possible that a problematic restriction enzyme site is introduced, and accordingly, the next frequently used nucleotide in the high-expression human genes can be used.

Preferably, the number of the codons for coding GCC alanine is increased in the codon-optimized apo-clytin-II nucleic acid of present invention, compared with in the wild-type jellyfish nucleic acid of SEQ ID NO: 2.

Herein, the so-called "increase in the number of codons" does not mean that there are more alanine amino acids than codon-optimized type; instead, it means that the relative number of codons for coding GCC alanine is greater than that of the codon-optimized apo-clytin-II nucleic acid. However, one can not exclude that there is a greater number of specific amino acids in the specific codon-optimized apo-clytin-II protein than that in the wild-type protein. For example, the codon-optimized apo-clytin-II protein can have a relatively greater number of amino acids, compared with the wild-type protein sequence of SEQ ID NO: 2.

By reference to the above definition, the codon-optimized apo-clytin-II nucleic acid of the present invention preferably includes one codon selected from the group consisting of codon for coding CGC arginine, codon for coding AAC asparagine, codon for coding GAC aspartic acid, codon for coding CAG glutamine, codon for coding GAG glutamic acid, codon for coding GGC glycine, codon for coding CAC histidine, codon for coding ATC isoleucine, codon for coding CTG leucine, codon for coding AAG lysine, codon for coding CCC proline, codon for coding TTC phenylalanine, codon for coding TCC or AGC serine, codon for coding TAC tyrosine, and codon for coding GTG valine, and the number of the one codon is greater than that of the wild-type jellyfish apo-clytin-II nucleic acid of SEQ ID NO: 2.

The human optimized apo-clytin-II with 7 amino acids added at the amino terminus is one of the preferred codon-optimized apo-clytin-II nucleic acids in the present invention. The codon-optimized nucleic acid of the present invention can be formed by fusing a codon-optimized apo-clytin-II nucleic acid and a nucleic acid for coding other proteins. As a result, the fusion protein can be expressed in the host cell having a control sequence for expressing the protein and the above sequence formed by the fusion. Furthermore, this result can be obtained for the N-terminus fusion protein or the C-terminus fusion protein.

The other proteins fused with the codon-optimized apo-clytin-II protein of the present invention are not particularly limited, and include, for example, secretion or other control sequence, tag sequence (e.g., 6-his tag), targeting sequence, and a green fluorescent protein that functions as a reporter protein. Additionally, HA 1 epitope, which functions as a recognition sequence, can be included, so that the expression and the determination of the concentration of apo-clytin-II protein can be achieved.

Another aspect of the present invention is a method for preparing a apo-clytin-II protein, which includes the steps of:

(i) preparing a recombinant expression vector that allows a codon-optimized apo-clytin-II nucleic acid to be under the control of a promoter that can function in host cells;

(ii) introducing the recombinant expression vector into an appropriate host cell; and (iii) allowing the host cell to express the codon-optimized apo-clytin-II protein.

In the preparation method of the present invention, the host cell is not particularly limited, and preferably a mammalian cell, in which case, the promoter is preferably a promoter that can function in mammals host cell.

The method of introducing the recombinant expression vector into the host cell is not particularly limited, and can be the methods described above or below. Furthermore, the method of expressing the codon-optimized apo-clytin-II protein is also not particularly limited, and includes, for example, culturing the host cell under the conditions suitable for expressing the codon-optimized apo-clytin-II protein.

Furthermore, the preparation method of the present invention can further include the step of:

(iv) purifying the expressed codon-optimized apo-clytin-II protein from a significant amount of other intracellular proteins.

After the step (iv), the purity of the codon-optimized apo-clytin-II protein is preferably 70% or more, 85% or more, and more preferably 95% or more.

Another aspect of the present invention is a method of enhancing the luminescence intensity of clytin-II, and the method includes introducing a nucleic acid into a host cell, in which the nucleic acid is formed by functionally combining a codon-optimized nucleic acid that codes and generates the apo-clytin-II protein with a control sequence that can achieve the effective expression of the nucleic acid.

In preferred embodiments, the nucleic acid containing the codon-optimized apo-clytin-II nucleic acid functionally combined with the control sequence is introduced into the host cell by means of transduction, transformation, or electroporation, etc. Further, the host cell is cultured under the conditions suitable for expressing the codon-optimized apo-clytin-II protein. "Enhancement of the luminescence intensity of clytin-II" refers herein to the increase in the luminescence intensity compared with the same expression system, except that the wild-type (non-humanized) jellyfish apo-aequorin gene is used.

Another aspect of the present invention is an application of a codon-optimized apo-clytin-II nucleic acid for enhancing the luminescence intensity of clytin-II in host cells.

Another aspect of the present invention is a method of determining the capability of a compound to block, inhibit, or antagonize a receptor upon activation, such as G-protein coupled receptor (hereinafter sometimes called GPCR) or ion channel, by the change of intracellular calcium ion. For example, GPCR can be expressed in a cell line, such as HEK293 cell or CHO cell, which is genetically engineered to express the codon-optimized apo-clytin-II protein. Before determination, the cells are incubated in the presence of coelenterazine; the generated apo-clytin-II thereby can be converted into clytin-II.

Specifically, the test compound is added into the cell, followed by adding a ligand. Further, the light emission generated by the increased calcium ion due to the activation of the receptor is determined with a standard luminometer. Then, in estimating the degree of inhibition by the test compound, the luminescence intensity from the cell treated by the compound is compared with the luminescence intensity from the cell treated by the ligand alone. Additionally, the clytin-II cell is treated by the test compound, and the amount of light emission is directly determined, so as to directly locate the receptor agonist.

Therefore, according to the aspect of the present invention, the receptor contained in the regulation of intracellular calcium and the mammalian cells operated in the manner that the clytin-II from the humanized gene is expressed are incubated with the test compound. Then, a coelenterazine cofactor is added, and the luminescence intensity is determined. The luminescence intensity herein is an indicator of the level of intracellular calcium that is released. Furthermore, the test result, that is, the capability of the test compound to inhibit or regulate the receptor can be recorded, for example, on paper or by electronic means.

The SEQ ID NOs: in the sequence list of the specification represent the following sequences, respectively.

[SEQ ID NO: 1] represents the amino acid sequence of the wild-type apo-clytin-II.

[SEQ ID NO: 2] represents the base sequence of the wild-type apo-clytin-II.

[SEQ ID NO: 3] represents the base sequence of the codon-optimized apo-clytin-II.

[SEQ ID NO: 4] represents the base sequence of the human-type clytin gene inserted into the expression vector pCMX-hCLII fabricated in Example 1.

[SEQ ID NO: 5] represents the amino acid sequence of the human-type clytin gene inserted into the expression vector pCMX-hCLII fabricated in Example 1.

[SEQ ID NO: 6] represents the base sequence of the human-type clytin gene inserted into the expression vector piP-H-hCLII fabricated in Example 2.

[SEQ ID NO: 7] represents the amino acid sequence of the human-type clytin gene inserted into the expression vector piP-H-hCLII fabricated in Example 2.

[SEQ ID NO: 8] represents the base sequence of the primer used in Example 2.

[SEQ ID NO: 9] represents the base sequence of the primer used in Example 2.

[SEQ ID NO: 10] represents the base sequence of the primer used in Example 2.

[SEQ ID NO: 11] represents the base sequence of the primer used in Example 2.

[SEQ ID NO: 12] represents the base sequence of the primer used in Example 2.

[SEQ ID NO: 13] represents the base sequence of the primer used in Example 2.

EXAMPLES

Hereinafter, the present invention is described in detail with the examples, but not limited to the examples.

Example 1

Design and Chemical Synthesis of the Codon-Optimized apo-clytin-II Nucleic Acid

The codon-optimized apo-clytin-II nucleic acid is designed in the following manner (Sequence list 3): without changing the amino acid sequence of apo-clytin-II, using the amino acid codon frequently used in human body, and converting the transcription factor recognition sequence into a non-activated sequence, removing the site that may be subjected to splicing, eliminating six restriction enzyme sites for base recognition, and without forming a palindrome sequence to make a loop structure. The codon usage frequency of the codon-optimized apo-clytin-II is shown in Table 2. Compared with the codon frequency of wild-type apo-clytin-II in Table 1, the codon-optimized apo-clytin-II nucleic acid is obviously an optimized design based on the humanized codon.

The optimized design codon-optimized apo-clytin-II nucleic acid of is synthesized by routine method and chemical synthesis. The cloning is performed in pBlueScript SK(+) (Stratagene Company) at the EcoRI/SalI restriction enzyme site to construct the pBlue-hCLII plasmid. The codon-optimized apo-clytin-II nucleic acid is confirmed by determining the base sequence with a DNA sequencer (manufactured by Applied Biosystems, ABI).

TABLE 2

Codon usage frequency of the codon-optimized clytin-II [Table 2]

| 1st base | 2nd base U | | 2nd base C | | 2nd base A | | 2nd base G | | 3rd base |
|---|---|---|---|---|---|---|---|---|---|
| U | TTT Phe | 0 | TCT Ser | 0 | TAT Tyr | 0 | TGT Cys | 0 | T |
|   | TTC | 13 | TCC | 0 | TAC | 4 | TGC | 3 | C |
|   | TTA Leu | 0 | TCA | 0 | TAA end | 0 | TGA end | 0 | A |
|   | TTG | 0 | TCG | 0 | TAG | 0 | TGG Trp | 6 | G |
| C | CTT | 0 | CCT Pro | 0 | CAT His | 0 | CGT Arg | 0 | T |
|   | CTC | 0 | CCC | 7 | CAC | 5 | CGC | 0 | C |
|   | CTA | 0 | CCA | 0 | CAA Gln | 0 | CGA | 0 | A |
|   | CTG | 14 | CCG | 0 | CAG | 4 | CGG | 0 | G |
| A | ATT Ile | 0 | ACT Thr | 0 | AAT Asn | 0 | AGT Ser | 0 | T |
|   | ATC | 11 | ACC | 8 | AAC | 8 | AGC | 11 | C |
|   | ATA | 0 | ACA | 0 | AAA Lys | 0 | AGA Arg | 5 | A |
|   | ATG Met | 4 | ACG | 0 | AAG | 17 | AGG | 0 | G |
| G | GTT Val | 0 | GCT Ala | 0 | GAT Asp | 0 | GGT Gly | 0 | T |
|   | GTC | 1 | GCC | 12 | GAC | 23 | GGC | 13 | C |
|   | GTA | 0 | GCA | 0 | GAA Glu | 0 | GGA | 0 | A |
|   | GTG | 6 | GCG | 0 | GAG | 14 | GGG | 0 | G |

Example 2

Construction of the Codon-Optimized apo-clytin-II Protein Expression Vector in Cultured Animal Cells The construction of the codon-optimized apo-clytin-II protein expression vector is as follows. Firstly, a novel expression vector pCMX-Linker is constructed in cultured animal cells. Specifically, in pCMX-GFP (described in Ogawa et al., (1995) PNAS. 92(25), 11899-11903), linkers Linker F(5)A-Sal (5' GT ACC ACC ATG CTC GAG CTG CAG GAA TTC TCT AGA G 3') (SEQ ID NO: 7) and Linker R(5)A-Sal (5' TC GAC TCT AGA GAA TTC CTG CAG CTC GAG CAT GGT G 3') (SEQ ID NO: 8) having a chemical synthesized multiple cloning sequence is inserted at the restriction enzyme site, i.e., the Asp718/SalI site, to construct the novel expression vector pCMX-Linker. That is, the novel expression vector is controlled by the CMV promoter, which has the Kozak sequence and multiple cloning site sequence (Asp71811 XhoI/PstI/EcoRI/XbaI/SalI/EcoRV/BamHI/MscI/NheI) in the downstream.

Thereafter, the codon-optimized apo-clytin-II protein expression vector using the novel expression vector pCMX-Linker is constructed as follows.

After digestion with the restriction enzyme EcoRI/SalI, with the routine method, pBlue-hCLII is linked to the EcoRI-SalI site of the pCMX-Linker, and the expression vector pCMX-hCLII is constructed as shown in FIG. 1. Further, the base sequence is determined by a DNA sequencer (manufactured by Applied Biosystems, ABI) to confirm the inserted DNA. Additionally, the control vector containing the wild-type apo-clytin nucleic acid as a control of the codon-optimized apo-clytin-II nucleic acid, i.e., pCMX-CLII, is constructed by the same method.

Example 3

Introduction of the Vector into Cells (1) Truncation and Purification of Expression Plasmid The pCMX-hCLII plasmid obtained in Example 2 is used to perform the following experiments. The pCMX-hCLII plasmid is purified in E. coli JM83 by using Endofree Plasmid Maxi kit (manufactured by QIAGEN Company), and then dissolved into sterilized water to a concentration of 1 µg/µl. Similarly, pCMX-hCLII and the firefly luciferase vector (pGL-control: Promega Company) applied as internal standard are used.

(2) Transfection

The cell line from human cervical cancer, i.e., HeLa line, is cultured with DMEM medium (with high-concentration glucose, Wako Chemicals) containing 10% fetal bovine serum (Invitrogen Company), and seeded in 6-well culture dish in $2 \times 10^5$ cells/well, and cultured in an incubator under the condition of 37° C. and 5% $CO_2$. After 24 hours, by using a FuGene HD transfection kit (Roche Company), the purified pCMX-hCLII plasmid is transfected into the HeLa cell in order to be used in the experiment. Specifically, 1 µl/µl of each of apo-clytin-II expression vector and the internal standard firefly luciferase expression vector and 6 µl FuGene HD are added into 100 µl of the DMEM medium, and the mixture is placed at room temperature for 15 min. 50 µl of solution of the DNA-FuGene complex is added to the cells in the six wells. After 24-h of culturing, the cells are washed with 2 ml of cold PBS for three times and 250 µl of cold PBS is added into the cells to recover the cells. The recovered cells are disintegrated with an ultrasonic homogenizer as an enzyme solution used for determination.

Example 4

Determination of Luminescent Activity in Cultured Animal Cells (1) Determination with Firefly Luciferase as Internal Standard 10 µl of the enzyme solution obtained in Example 3 is added into 50 µl of the enzyme assay reagent (Promega Company) to initiate the luminous reaction. The luminescent activity is determined by a luminescence measuring device (AB2200, manufactured by Atto Company) for 10 seconds and expressed in relative luminescence intensity.

(2) Determination of Luminescent Activity

50 µl of the enzyme solution obtained in Example 3 is added into 950 µl of 50 mM Tris-HCl (pH 7.6) containing 1 µl of mercaptoethanol (Wako Chemicals), 1 µl of coelenterazine (manufactured by Chisso Company), and 10 mM of EDTA (Wako Chemicals), and the resulting mixture is placed at 4° C. for 3 h for the regeneration of clytin-II to occur. 50 mM Tris-HCl (pH 7.6) solution containing 100 µl of 50 mM $CaCl_2$ is added into 10 µl of the regenerated solution in order for the regenerated solution to emit light. The light emission is determined by a luminescence measuring device (AB2200, manufactured by Atto Company) for 10 seconds, and the maximum luminescence intensity is expressed by relative luminescence value.

The results are summarized in Table 3. The activation rate is calculated according to the activity of firefly luciferase used as the internal standard. According to the results, the codon-optimized clytin-II protein of the present invention exhibits an activity of about 15 times or more, compared with the wild-type apo-clytin-II.

TABLE 3

Comparison of expression of the wild-type clytin-II gene and the human-type clytin-II gene in cultured cells

| Used plasmid | Clytin-II luminescent activity (rlu) | Firefly luciferase activity (rlu) | Clytin-II luminescent activity/firefly luciferase activity (×1000) | Activation rate |
|---|---|---|---|---|
| — | 24 | 100 | — | — |
| pCMX-CLII + pGL-control | 1504 | 255724 | 5.8 | 1.0 |
| pCMX-hCLII + pGL-control | 21892 | 187976 | 116.4 | 15.8 |

Example 5

Construction of Codon-Optimized clytin-II Protein Expression Vector in E. coli

In order to express the codon-optimized apo-clytin-II nucleic acid in E. coli, the expression vector piP-H-L(6) is constructed as the starting material. Specifically, the linker having a chemical synthesized multiple cloning sequence H/P/S/Xb/Xh/B:Linker-F (5' AG CTT CTG CAG GTC GAC TCT AGA CTC GAG G 3') (SEQ ID NO: 9) and H/P/S/Xb/Xh/B:Linker-R (5' GA TCC CTC GAG TCT AGA GTC GAC CTG CAG A 3') (SEQ ID NO: 10) is inserted at the HindIII-BamHI site of the piP-(His6)HE vector, as described in Japanese Patent Publication 2008-22848, to construct piP-H-L(6). The basic vector piP-H-L(6) is controlled by the E. coli lipoprotein promoter and the lactose operon, which has an OmpA sequence for secretion, a six histidine sequence for purification with chelate gel, and various multiple cloning sequences.

Figure 2:
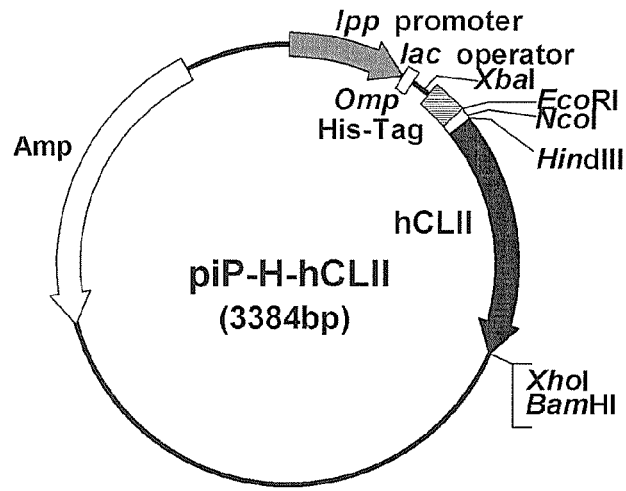
FIG. 2 is a schematic diagram of the codon-optimized apo-clytin-II protein expression vector piP-H-hCLII in prokaryotic organisms used in the present invention.

The construction of the codon-optimized apo-clytin-II protein expression vector using the basic vector piP-H-L(6) is as follows. With pBlue-hCLII as template, PCR is performed by using the PCR primer pair: hCLII-1N/HindIII (5' ggc aagctt GTG AAG CTG GAC CCC GAC TTC 3') (SEQ ID NO: 11) and hCLII-2C/XhoI (5' ggc CTCGAG TTA GGG GAC GAA GTT GCC GTA 3') (SEQ ID NO: 12) with a PCR kit (manufactured by Nippon Gene Company) (cycling conditions: 25 cycles; 1 min/94° C., 1 min/50° C., 1 min/72° C.). The obtained segment is purified with a PCR purification kit (manufactured by Qiagen Company), digested with the restriction enzyme HindIII/XhoI, and then inserted into the restriction enzyme HindIII/XhoI site of piP-H-L(6) to construct the expression vector piP-H-hCLII as shown in FIG. 2. Further, the base sequence is determined with a DNA sequencer (manufactured by Applied Biosystems Company, ABI) to confirm the inserted DNA.

Example 6

Expression of Codon-Optimized apo-clytin-II Protein in E. Coli

In order to express the codon-optimized apo-clytin-II protein (hereinafter sometimes called "hCLII") in E. coli, the recombinant plasmid piP-H-hCLII fabricated in Example 2 is used. The recombinant plasmid piP-H-hCLII is introduced into the E. coli strain WA802 by routine methods, and the obtained transformant is implanted into a 10 ml Luria-Bertani (LB) liquid medium (10 g bacto tryptone, 5 g yeast extract, and 5 g NaCl contained in each liter water, pH 7.2) containing ampicillin (50 µg/ml), and cultured at 30° C. for 18 h. Then, the culture is added into a new LB liquid medium 400 ml×5 (total amount 2 L), and cultured at 30° C. for 18 h. After culturing, the bacteria are centrifuged for recovery (5,000 rpm, 5 min), and the cultured bacteria after collection is used as a starting material for protein extraction.

Example 7

Extraction and Purification of Codon-Optimized apo-clytin-II Protein from Cultured Bacteria The cultured bacteria after collection is suspended in 200 ml of 50 mM Tris-HCl (pH 7.6), cooled in an ice bath, and subjected to an ultrasonic treatment (manufactured by Branson Company, Sonifier model cycle 250) for 3 min for 3 times, and the disintegrated bacteria liquid is centrifuged at 10,000 rpm (12,000×g) at 4° C. for 20 min. The obtained soluble fraction is supplied to a nickel-chelated column (Amersham biosciences Company, column size: diameter 2.5 cm×6.5 cm) balanced by 50 mM Tris-HCl (pH 7.6), to allow the codon-optimized apo-clytin-II protein to be adsorbed. After being washed with 500 ml of 50 mM Tris-HCl (pH 7.6), the codon-optimized apo-clytin-II protein is eluted with 0.1 M imidazole (manufactured by Wako Chemicals Company). With bovine serum albumin (manufactured by Pias Company) as sample, the concentration of the purified protein is determined by a commercially available kit (manufactured by Bio-Rad Company) according to the Bradford method. As a result, 45.7 mg codon-optimized apo-clytin-II protein is obtained from 2 L of cultured bacteria. The purification is determined to be 95% or more by the SDS-PAGE analysis.

Example 8

Determination of Luminescent Activity

The light emission of clytin-II during purification is determined in the following manner, wherein clytin-II is constructed with codon-optimized apo-clytin-II protein as a component. After 2-mercaptoethanol (1 µl) and substrate coelenterazine (1 µg/µl) dissolved in ethanol are blended into 990 µl of 30 mM Tris-HCl (pH 7.6) containing 10 mM EDTA, 10 µl of human-type apo-clytin-II solution is added, and placed on ice (4° C.) for 2 h. 100 µl of 50 mM calcium solution is added into 10 µl of regenerated human-type clytin-II solution to initiate the luminous reaction. The luminescent activity is determined with a luminescence measuring device (AB2200, manufactured by Atto Company) by determining the light emission for 10 seconds. The maximum luminescence intensity is expressed by the relative luminescence value (Table 4).

TABLE 4

Purification yield of codon-optimized apo-clytin-II protein

| Stage | Total amount (ml) | Total amount of protein (mg) | Total activity (×10⁹rlu) | Specific activity (×10⁹/mg) | Recovery rate (%) Protein | Recovery rate (%) Activity |
|---|---|---|---|---|---|---|
| Crude extract | 200 | 720 | 89.3 | 1.2 | 100 | 100 |
| Nickel chelate gel | 30 | 45.7 | 59.2 | 27.8 | 6.3 | 66 |

INDUSTRIAL APPLICABILITY

The codon-optimized nucleic acid for coding apo-clytin-II is introduced into a host cell to get the codon-optimized apo-clytin-II protein. When forming the complex consisting of the codon-optimized apo-clytin-II protein, the luminescent substrate and molecular oxygen, the codon-optimized apo-clytin-II protein exhibits a more significant luminescent activity than that using the wild-type apo-clytin-II. Furthermore, the clytin-II fabricated by the present invention is very effective in various applications, such as the detection of intracellular calcium change.

SEQUENCE LISTING

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A codon-optimized nucleic acid, for coding apo-clytin-II protein, wherein the codon-optimized nucleic acid is SEQ ID NO:3 expressed by an expression vector/host systems comprising mammalian cells, bacteria cells, or yeast cells.

2. A codon-optimized nucleic acid, formed by fusing the codon-optimized nucleic acid according to claim 1 with a nucleic acid that codes other proteins.

3. An expression vector, comprising a codon-optimized nucleic acid for coding an apo-clytin-II protein wherein said codon optimized nucleic acid is SEQ ID NO:3 and wherein said codon-optimized nucleic acid is under a regulatory control of a promoter that functions in mammalian cells and is expressed by an expression vector/host systems selected from the group comprising mammalian cells, bacteria cells, or yeast cells.

4. The expression vector according to claim 3, comprising the codon-optimized nucleic acid for coding the apo-clytin-II protein, and a regulatory sequence for controlling an expression of the codon-optimized nucleic acid for coding the apo-clytin-II protein in the mammalian cells.

5. A recombinant host cell selected from the group comprising mammalian cells, bacteria cells or yeast cells, wherein said recombinant host cell comprises a codon-optimized nucleic acid according to claim 1 for coding an apo-clytin-II protein.

* * * * *